(12) United States Patent
Shih et al.

(10) Patent No.: US 10,673,663 B2
(45) Date of Patent: Jun. 2, 2020

(54) PHYSIOLOGICAL INFORMATION COLLECTING SYSTEM AND TRANSCEIVER DEVICE THEREOF

(71) Applicant: Tamkang University, New Taipei (TW)

(72) Inventors: Horng-Yuan Shih, New Taipei (TW);
Yu-Chuan Chang, New Taipei (TW);
Cheng-Wei Yang, New Taipei (TW)

(73) Assignee: TAMKANG UNIVERSITY, New Taipei (TW)

( * ) Notice: Subject to any disclaimer, the term of this patent is extended or adjusted under 35 U.S.C. 154(b) by 120 days.

(21) Appl. No.: 15/958,128

(22) Filed: Apr. 20, 2018

(65) Prior Publication Data
US 2019/0238376 A1    Aug. 1, 2019

(30) Foreign Application Priority Data

Feb. 1, 2018 (TW) .............................. 107103699 A (51) Int. Cl.
*H04L 27/20* (2006.01)
*H03L 7/107* (2006.01)
(Continued)

(52) U.S. Cl.
CPC .......... *H04L 27/2082* (2013.01); *A61B 5/002* (2013.01); *H03L 7/1072* (2013.01); *H04L 27/2331* (2013.01)

(58) Field of Classification Search
CPC ....... H04L 27/0012; H04L 1/00; H04L 27/22; H04L 27/26; H04L 5/00; H04L 27/2003; H04L 27/2025; H04L 27/2082; H04L 27/2331; H04L 27/2334; H04L 5/0007; H04L 1/1692; H04L 1/1812; H04L 27/2275; H04L 5/023; G01S 19/37; G01S 19/44; G01S 3/146; G01S 3/46; G01S 7/52033; G01S 7/5205; G01S 7/52077;
(Continued)

(56) References Cited

U.S. PATENT DOCUMENTS

2016/0018509 A1* 1/2016 McCorkle ............... G01S 3/146
  342/386
2019/0222264 A1* 7/2019 Frederick ............. H04B 5/0031

* cited by examiner

*Primary Examiner* — Yemane Mesfin
*Assistant Examiner* — Mon Cheri S Davenport
(74) *Attorney, Agent, or Firm* — Birch, Stewart, Kolasch & Birch, LLP (57) ABSTRACT

A physiological information collecting system and a transceiver device thereof are configured to collect physiological information from animal bodies. The transceiver device includes a front-end circuit, a follower circuit, a quadrature delay line and an output circuit. The front-end circuit separates a discontinuous signal into an in-phase signal and a quadrature signal. The follower circuit outputs a control voltage and rotates the in-phase signal by a predetermined phase angle to output a follower signal. The quadrature delay line rotates the quadrature signal by a corresponding phase angle according to the control voltage. The output circuit synthesizes the follower signal and the quadrature signal and outputs a data signal by demodulating the discontinuous signal. Consequently, the transceiver device reduces the bandwidth range of the discontinuous signal when receiving the discontinuous signal, reduces the power consumed by the transceiver device, and demodulates the discontinuous signal with various transmission rates of different data.

24 Claims, 5 Drawing Sheets

(51) Int. Cl.
*A61B 5/00* (2006.01)
*H04L 27/233* (2006.01)

(58) Field of Classification Search
CPC ...... H01Q 21/24; H01Q 21/29; H03D 7/1458;
H03D 2200/0082; H03D 3/008; H03D
7/165; H03D 7/166; H03D 3/04; H03G
3/3052; H03G 3/3078; H03G 3/3068;
H04B 5/0062; H04B 7/01; B01D
2201/52; B01D 27/10; B01D 35/14;
B01D 46/009; H04W 52/52; A61B 5/002;
A61B 5/0245; A61B 5/04005; A61B
5/04017; A61B 5/0456; A61B 5/4035;
A61B 5/415; A61B 5/418; A61B 5/4836;
A61B 5/4884; A61B 8/06; A61B 8/08;
A61B 8/14; A61B 8/4444; A61B 8/465;
A61B 8/467; A61B 8/488; A61B 8/5207;
A61B 8/5276; A61B 8/54; H03C 1/547;
H03L 7/1072; H03L 7/0812; H03L
7/0814; H03L 7/087; G01R 23/10; G01R
23/167; G11B 20/10009; G11B 5/012;
H03J 7/04; H03M 1/14; H03M 1/502;
H03M 1/60

See application file for complete search history.

PHYSIOLOGICAL INFORMATION COLLECTING SYSTEM AND TRANSCEIVER DEVICE THEREOF

CROSS-REFERENCE TO RELATED APPLICATION

This non-provisional application claims priority under 35 U.S.C. § 119(a) to Patent Application No. 107103699 filed in Taiwan, R.O.C. on Feb. 1, 2018, the entire contents of which are hereby incorporated by reference.

BACKGROUND

Technical Field

This disclosure generally relates to a physiological information collecting system and a transceiver device thereof.

Related Art

Detection devices can be worn on the human body or implanted in the human body to detect various physiological signals of the human body or to release drugs. Such detection devices include, for example, hydrogen sulfide detectors, occult blood detectors, heart rate monitors, blood pressure meters, etc. Additionally, detection devices can be connected to external devices (such as smart bracelets and medical devices) to transmit data signals (such as physiological signals, control signals, etc.) bidirectionally between the detection devices and an external devices. For example, when a detection device transmits a data signal by wireless communication, typically the data signal is first modulated into a radio frequency (RF) signal (or a modulated signal) and then the RF signal is transmitted. The external devices receive and demodulate the RF signal to obtain a data signal from the RF signal. For wireless communication, the available radio bandwidth has gradually been reduced, and most current RF signals are continuous signals with a narrower bandwidth, which is relatively limited.

SUMMARY

In view of this problem, one embodiment of this disclosure provides a physiological information collecting system including a detection device and a transceiver device. The detection device includes a detection module configured to detect a data signal and a communication module configured to modulate the data signal into a discontinuous signal and transmit the discontinuous signal. The transceiver device includes a front-end circuit configured to receive and amplify the discontinuous signal and separate the discontinuous signal amplified into an in-phase baseband signal and a quadrature baseband signal that are orthogonal to each other. The follower circuit is configured to output a control voltage and configured to rotate the in-phase baseband signal by a phase angle to output a follower signal. The follower signal follows the in-phase baseband signal, and the control voltage corresponds to a phase angle difference between the follower signal and the in-phase baseband signal. The quadrature delay line is configured to rotate the quadrature baseband signal by a corresponding phase angle according to the control voltage. The corresponding phase angle is the phase angle difference plus 90 degrees. The output circuit is configured to synthesize the follower signal and the quadrature baseband signal rotated and output the data signal. Consequently, the detection device and the transceiver device are adapted to transmit the discontinuous signal to reduce the power consumption and simplify the circuit configurations of the detection device and the transceiver device. Additionally, the detection device and the transceiver device reduce the bandwidth range of the discontinuous signal when transmitting the discontinuous signal, reduce the power consumed by the detection device and the transceiver device, and demodulate the discontinuous signal with various transmission rates of different data.

Another embodiment of this disclosure provides a transceiver device capable of receiving or transmitting a discontinuous signal through a human body passage. The transceiver device includes a front-end circuit, a follower circuit, a quadrature delay line and an output circuit. The front-end circuit is configured to receive and amplify a discontinuous signal and separate the discontinuous signal amplified into an in-phase baseband signal and a quadrature baseband signal that are orthogonal to each other. The follower circuit is configured to output a control voltage and configured to rotate the in-phase baseband signal by a phase angle to output a follower signal. The follower signal follows the in-phase baseband signal, and the control voltage corresponds to a phase angle difference between the follower signal and the in-phase baseband signal. The quadrature delay line is configured to rotate the quadrature baseband signal by a corresponding phase angle according to the control voltage. The corresponding phase angle is the phase angle difference plus 90 degrees. The output circuit is configured to synthesize the follower signal and the quadrature baseband signal rotated and output a data signal. Consequently, the detection device and the transceiver device are adapted to transmit the discontinuous signal to reduce the power consumption and simplify the circuit configurations of the detection device and the transceiver device. Additionally, the detection device and the transceiver device reduce the bandwidth range of the discontinuous signal when transmitting the discontinuous signal, reduce the power consumed by the detection device and the transceiver device, and demodulate the discontinuous signal with various transmission rates of different data.

Another embodiment of this disclosure provides a physiological information collecting system including a portable electronic device and a wearable electronic device. The portable electronic device includes a touch element configured to generate a touch signal and a communication interface configured to transmit a discontinuous signal according to the touch signal. The wearable electronic device includes: a front-end circuit configured to receive and amplify the discontinuous signal transmitted by the communication interface and separate the discontinuous signal amplified into an in-phase baseband signal and a quadrature baseband signal that are orthogonal to each other; a follower circuit configured to output a control voltage and configured to rotate the in-phase baseband signal by a phase angle to output a follower signal, the follower signal following the in-phase baseband signal, and the control voltage corresponding to a phase angle difference between the follower signal and the in-phase baseband signal; a quadrature delay line configured to rotate the quadrature baseband signal by a corresponding phase angle according to the control voltage, the corresponding phase angle being the phase angle difference plus 90 degrees; and an output circuit configured to synthesize the follower signal and the quadrature baseband signal rotated and output the data signal. Consequently, the detection device and the transceiver device are adapted to transmit the discontinuous signal to reduce the power consumption and simplify the circuit configurations of the detection device and the transceiver device. Additionally, the detection device and the transceiver device reduce the bandwidth range of the discontinuous signal when transmitting the discontinuous signal, reduce the power consumed by the detection device and the transceiver device, and demodulate the discontinuous signal with various transmission rates of different data.

BRIEF DESCRIPTION OF THE DRAWINGS

This disclosure will become more fully understood from the detailed description given herein below for illustration only, and thus not limitative of this disclosure, wherein.

DETAILED DESCRIPTION

Figure 1:
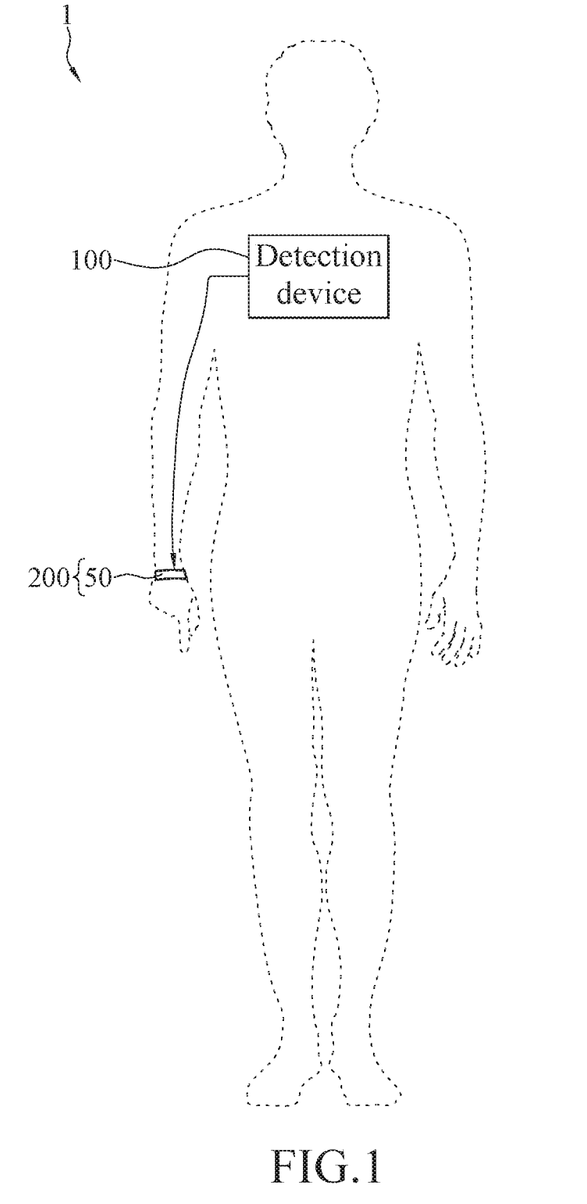
FIG. 1 illustrates an exemplary application of a physiological information collecting system according to a first embodiment of this disclosure.
Figure 2:
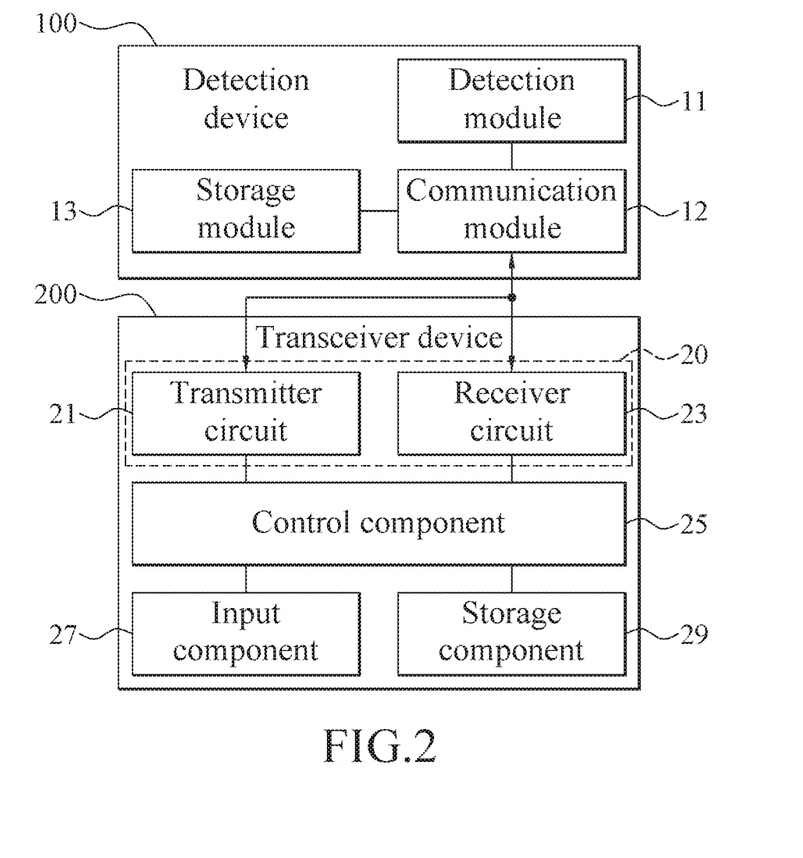
FIG. 2 illustrates a schematic block diagram of a physiological information collecting system according to a first embodiment of this disclosure.

With reference to FIG. 1 and FIG. 2, the first embodiment of this disclosure provides a physiological information collecting system 1 including a detection device 100 and a transceiver device 200. The detection device 100 can be an electronic device capable of detecting physiological information, for example, a hydrogen sulfide detector, an occult blood detector, a heart rate monitor, a blood pressure meters, a portable ultrasound diagnostic device, etc. The detection device 100 includes a detection module 11 and a communication module 12. The detection module 11 (for example, a bio-sensor) can detect a data signal (for example, physiological information of a human body). The communication module 12 modulates the data signal into a modulated signal and transmits the modulated signal to the transceiver device 200.

With reference to FIG. 2, in one embodiment, the detection device 100 further includes a storage module 13 configured to store the data signal detected by the detection module 11. The storage module 13 can be a non-volatile memory or a hard disk. The transceiver device 200 further includes a storage component 29 configured to store the data signal received by a communication interface 20. The storage component 29 and storage module 13 have similar hardware configurations and thus detailed descriptions thereof are not repeated herein.

Figure 5:
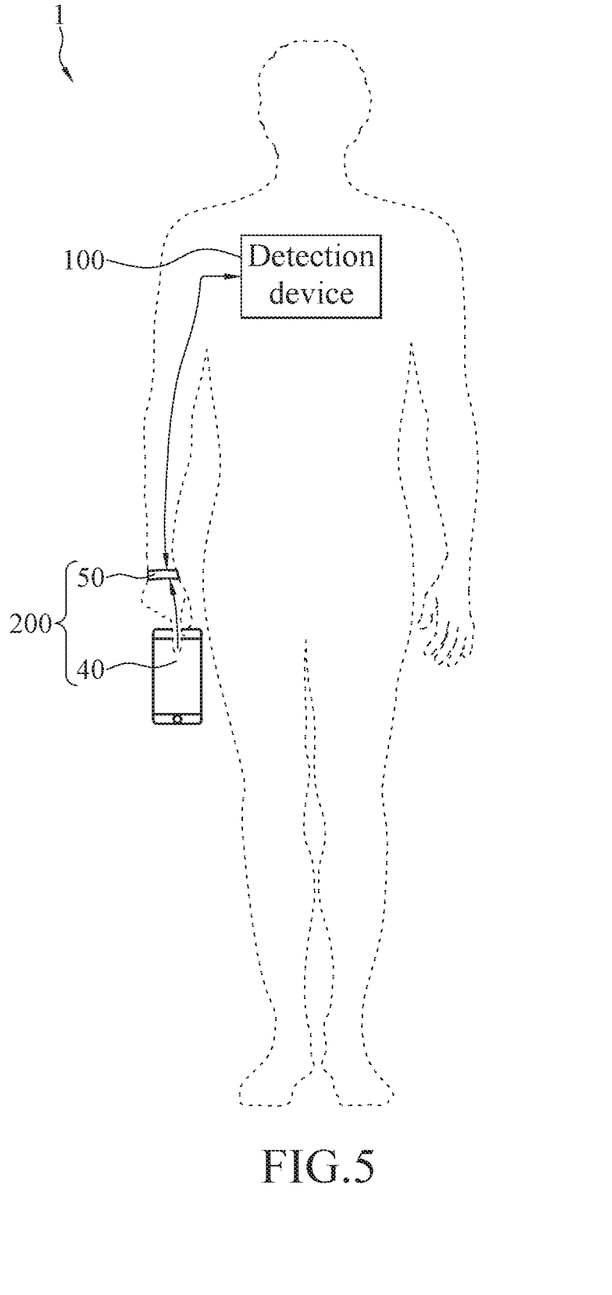
FIG. 5 illustrates an exemplary application of a physiological information collecting system according to a second embodiment of this disclosure.

With reference to FIG. 1, FIG. 2 and FIG. 5, the transceiver device 200 can be implemented by using a portable electronic device 40 (for example, a smart phone, a tablet computer or a portable ultrasound diagnostic device) a wearable electronic device 50 (for example, a smart bracelet or a smart watch) or other electronic devices capable of receiving or transmitting modulated signals. The transceiver device 200 includes a communication interface 20 and a control component 25 connecting to the communication interface 20. After the communication interface 20 receives the modulated signal, the communication interface 20 demodulates the data signal in the modulated signal. Then, the control component 25 drives the communication interface 20 to modulate a sleep signal into a modulated signal, and the communication interface 20 transmits the modulated signal to the communication module 12 of the detection device 100. When the communication module 12 of the detection device 100 demodulates the sleep signal in the modulated signal, the detection module 11 stops transmitting the modulated signal containing the data signal according to the sleep signal.

The modulated signal indicates a modulated signal generated by modulating a binary signal (containing, for example, physiological information). Such modulated signal may be, for example, the frequency shift keying (FSK) the phase shift keying (PSK) or the amplitude shift keying (ASK) modulated signal. Additionally, the modulated signal may be continuous or discontinuous. The bandwidth of the modulated signal is within a range from 3 KHz to 800 MHz, where low bandwidth is ranging from 3 KHz to 300 KHz, middle bandwidth is ranging from 300 KHz to 3 MHz and high bandwidth is ranging from 3 MHz to 300 MHz. Taking a discontinuous FSK signal as an example, the bandwidth of a discontinuous FSK signal is within a range from 1 MHz to 40 MHz. The term "bandwidth" described in this specification only serves to illustrate these embodiments of this disclosure. The bandwidth of a substantially modulated signal depends on the type of data signal, such as an audio signal, a video signal or a medical image, and is not intended to limit the scope of this disclosure.

With reference to FIG. 2, in one embodiment, the control unit 25 of the transceiver 200 can drive the transmitting circuit 21 to transmit a discontinuous signal containing a wake-up signal or drive the receiving circuit 23 to receive a discontinuous signal containing a data signal according to a schedule. In one embodiment, the transceiver device 200 further includes an input component 27, such as a user interface, a button, a sound input component and so on, configured to generate a trigger signal. Accordingly, the control component 25 drives the transmitter circuit 21 to transmit a discontinuous signal containing a wake-up signal or drives the receiver circuit 23 to receive a discontinuous signal containing a data signal according to the trigger signal.

In one embodiment, the communication interface 20 of the transceiver device 200 can obtain the identification (ID) number of the detection device 100 via a protocol such as TCP, HTTP, SSL, or the like. Conversely, the communication module 12 of the detection device 100 may also obtain the ID number of the transceiver device 200 via a protocol. In other words, the transceiver device 200 and the detection device 100 establish a connection to each other through a handshake process. The term "connection" described in this specification only serves to explain the connection or interaction between various elements in the drawings via the Internet or the human body passage between the transceiver device 200 and the detection device 100, and is not intended to limit the scope of this disclosure.

Figure 3:
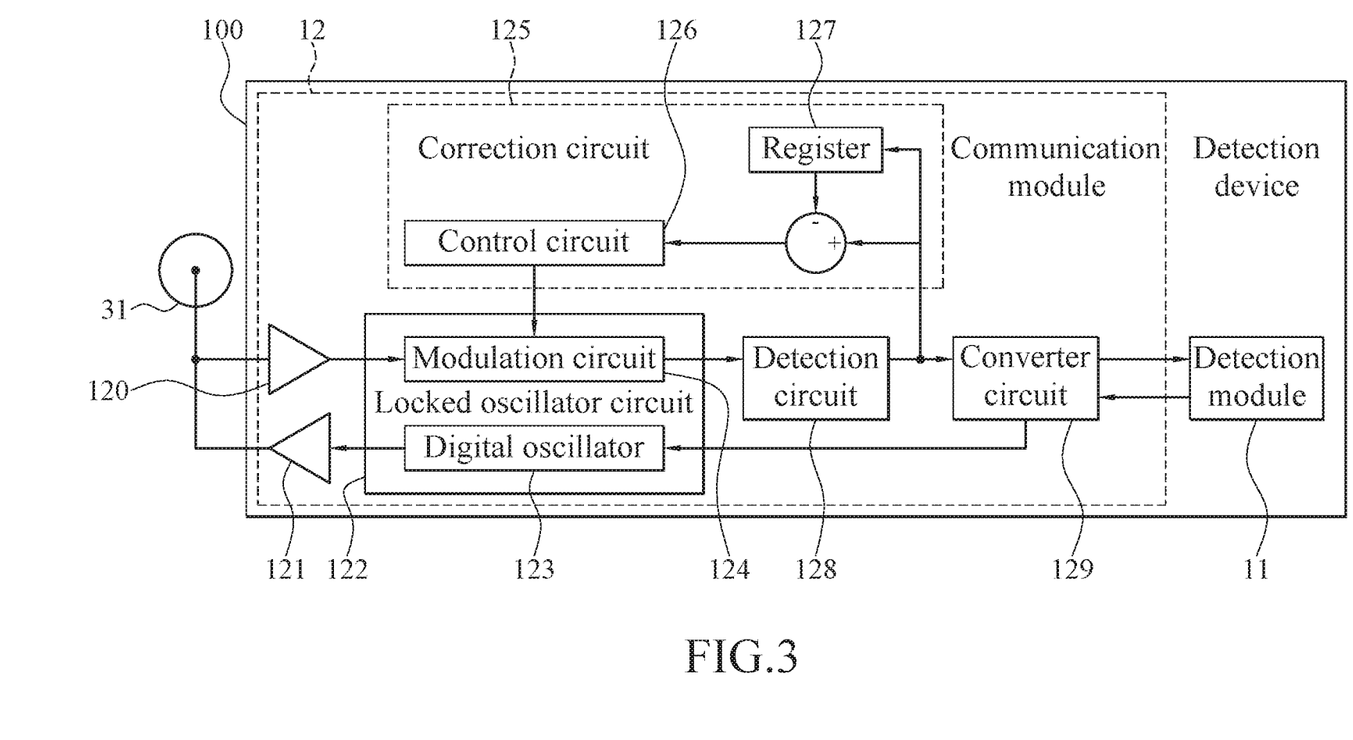
FIG. 3 illustrates a schematic block diagram of a detection device in FIG. 1.
Figure 4:
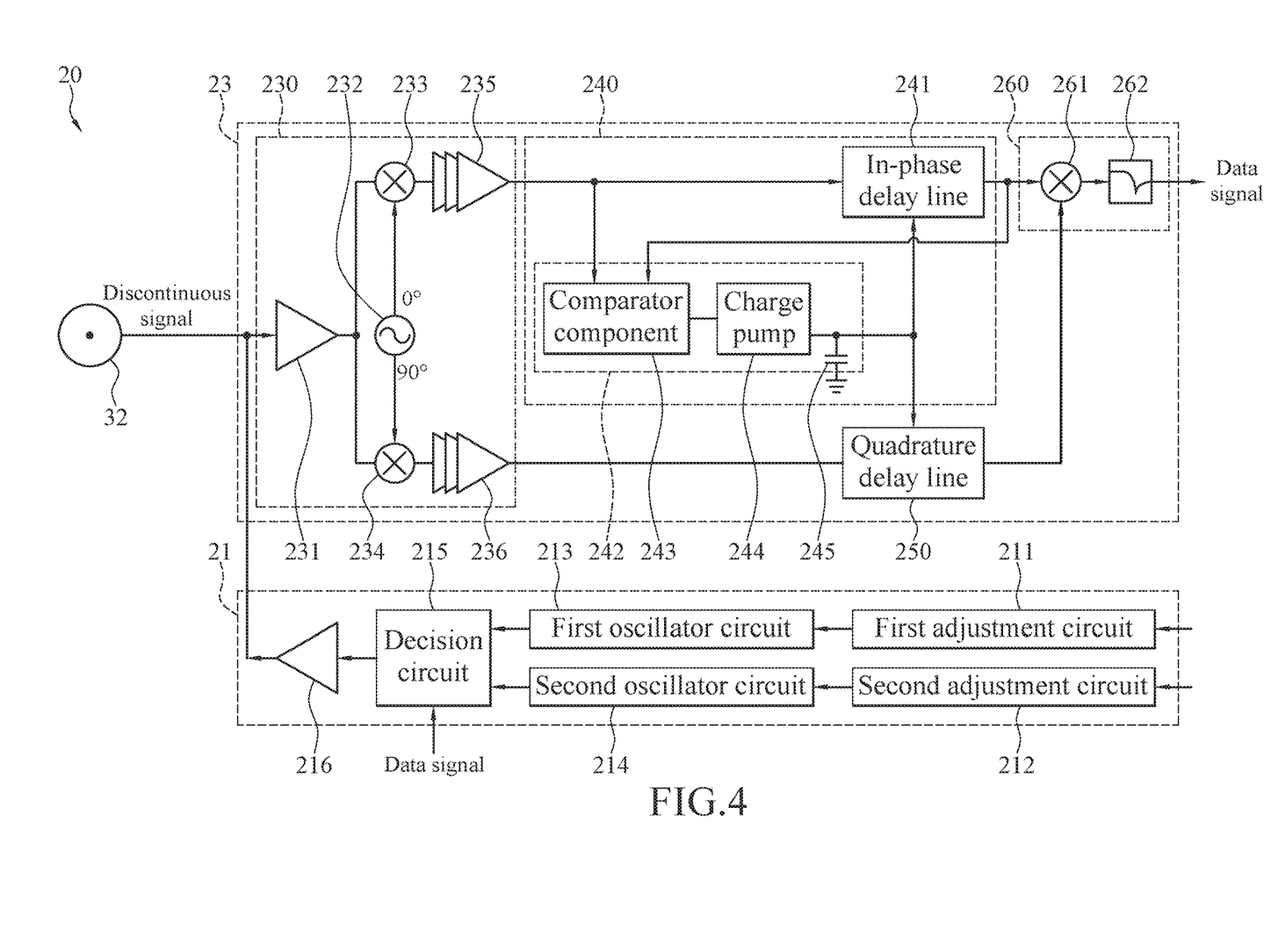
FIG. 4 illustrates a schematic block diagram of a transceiver device in FIG. 1.

With reference to FIG. 3 and FIG. 4, in one embodiment, the detection device 100 includes a first touch element 31 (for example, an electrode plate) electrically connected to the communication module 12. The transceiver device 200 includes a second touch element 32 electrically connected to the communication interface 20. The touch element (for example, the first touch element 31 and the second touch element 32) can be implemented using a copper foil or an electrode plate configured to be touched by the human skin to form a human body passage. When the first touch element 31 and the second touch element 32 are touched by the human skin, a human body passage is established between the first touch element 31 and the second touch element 32 via the human skin. The term "connection" described in this specification can be an electrical connection or a communication connection. The electrical connection connects two objects (such as devices or elements) with two ends of a conductive wire respectively to transmit or receive a modulated signal. The communication connection uses the air or a human body passage as a bridge having two ends respectively connected to two objects (such as devices or elements) to transmit or receive a modulated signal. Additionally, the communication module 12 of the detection device 100 can transmit or receive a discontinuous signal via the human body passage, and the communication interface 20 of the transceiver device 200 can transmit or receive the discontinuous signal via the human body passage. The term "discontinuous signal" described in this specification may refer to the modulated signal of "data signal," "wake-up signal," "sleep signal," "trigger signal," or other control signals and only serves to explain the connection or interaction between various elements in the drawings, and is not intended to limit the scope of this disclosure.

Taking a smart bracelet as an example, the smart bracelet includes a user interface (such as a touch panel) a communication interface 20, a second touch element 32, and a control component 25 connecting the second touch element 32, the communication interface 20 and the user interface. When the first touch element 31 of the detection device 100 and the second touch element 32 of the smart bracelet are touched by the human skin, a human body passage is formed between the smart bracelet and the detection device 100. When a user touches a touch panel (such as a capacitive touch panel) the position where the touch panel is touched by the user corresponds to one or more capacitors with a current variation. Based on the capacitors, the control component 25 executes an application corresponding to the position where the touch panel is touched. The application drives the communication interface 20 to transmit a wake-up signal to the communication module 12 of the detection device 100 via the human body passage. The communication module 12 transmits the data signal detected by the detection module 11 to the communication interface 20 according to wake-up signal. Next, after the communication interface 20 receives the data signal, the control component 25 drives the communication interface 20 to transmit a sleep signal to the communication module 12 of the detection device 100 to stop the communication module 12 from transmitting the data signal.

Taking a smart phone as an example, the smart phone includes a user interface (such as a wave-based touch screen) a communication interface 20, a second touch element 32 and a control component 25 connecting the user interface, the communication interface 20 and the second touch element 32. When the first touch element 31 of the detection device 100 and the second touch element 32 of the smart phone are touched by the human skin, a human body passage is formed between the smart phone and the detection device 100. The wave-based touch screen uses ultrasonic transmitters and receivers installed around the touch panel to transmit and receive ultrasonic waves to and from each other. When the user's finger touches the touch panel, the transmitted ultrasonic wave is blocked by the finger, causing the transmitted ultrasonic wave to attenuate. The control component 25 compares the ultrasonic attenuation variation before and after the ultrasonic wave is blocked to calculate the position where the touch panel is touched, and the position corresponds to the communication interface 20. When the control component 25 determines that the touched position corresponds to the communication interface 20, the control component 25 drives the communication interface 20 to transmit a wake-up signal to the communication module 12 of the detection device 20. The communication module 12 transmits the data signal detected by the detection module 11 to the communication interface 20 according to the wake-up signal. Then, after the communication interface 20 receives the data signal, the control component 25 drives the communication interface 20 to transmit a sleep signal to the communication module 12 of the detection device 100 to stop the communication module 12 from transmitting the data signal.

In one embodiment, when the user touches the second touch element 32 of the smart phone and the touch panel, the smart phone and the touch panel may be connected to each other via the human body passage. When the control component 25 or the communication interface 20 of the smart phone receives a trigger signal, the control component 25 transmits a wake-up signal to the touch panel via the human body passage according to the trigger signal. The plurality of array capacitors in the touch panel may couple the transmitted wake-up signal via the human body passage. That is, the touch panel may receive the transmitted wake-up signal via the human body passage. Similarly, the touch panel can also receive the data signal transmitted from the smart phone via the human body passage.

With reference to FIG. 2 and FIG. 3, the communication module 12 includes a first amplifier 120, a second amplifier 121, a locked oscillator circuit 122, a correction circuit 125, a detection circuit 128 and a converter circuit 129. Additionally, the first amplifier 120, such as a low-noise amplifier, can receive and amplify a wake-up signal modulated by FSK (such as a FSK modulated signal). The second amplifier 121, such as a power amplifier, may transmit a data signal modulated by FSK after the low-noise amplifier receives the FSK modulated signal. The locked oscillator circuit 122, such as an injection-locked digitally controlled oscillator, includes a digital oscillator 123 and a modulation circuit 124. The digital oscillator 123 can adjust the predetermined frequency of the data signal. The modulation circuit 124 converts the FSK signal into an ASK signal. The correction circuit 125, such as a digital auxiliary injection-locked frequency correction circuit, includes a control circuit 126 and a register 127. According to the level of the ASK signal detected by the detection circuit 128, the control circuit 126 locks the frequency of the ASK signal by a gradient ascent algorithm to a predetermined bandwidth (for example, 20 MHz) and generates a digital control signal (for example, a correction signal at a frequency of 40 MHz). The modulation circuit 124 then corrects the level of the ASK signal according to the FSK signal and the digital control signal. The register 127 stores a level of the ASK signal detected by the detection circuit 128 a previous time. The detection circuit 128, such as a peak detector, can detect the level of the ASK signal. The converter circuit 129, such as an analog-to-digital converter circuit, can convert the ASK signal into a data signal.

With reference to FIG. 2 and FIG. 4, the transceiver device 200 includes a communication interface 20. The communication interface 20 includes a transmitter circuit 21, a receiver circuit 23 and a control component 25 connecting the transmitter circuit 21 and the receiver circuit 23. For example, the transmitter circuit 21 can transmit a discontinuous signal containing a wake-up signal to drive the communication module 12 of the detection device 100 to transmit a discontinuous signal containing a data signal. The receiver circuit 23 can receive the discontinuous signal containing the data signal transmitted by the communication module 12 and demodulate the data signal in the discontinuous signal containing the data signal. After the receiver circuit 23 demodulates the data signal in the discontinuous signal containing the data signal, the control component 25 drives the transmitter circuit 21 to transmit a discontinuous signal containing a sleep signal to drive the communication module 12 of the detection device 100 to stop from transmitting a discontinuous signal containing a data signal and controls the detection device 100 to be in a sleep state. The term "sleep state" refers to stopping the detection module 11 from detecting physiological information of the human body and the communication module 12 from transmitting the discontinuous signal containing the data signal, while only the communication module 12 keeps receiving the wake-up signal.

In one embodiment, the communication module 12 of the detection device 100 may also be the communication interface 20 of the transceiver device 200. In one embodiment, the communication interface 20 of the transceiver device 200 may also be the communication module 12 of the detection device 100.

With reference to FIG. 1, FIG. 2 and FIG. 4, the transmitter circuit 21 includes a first adjustment circuit 211, a second adjustment circuit 212, a first oscillator circuit 213, a second oscillator circuit 214, a decision circuit 215 and a transmitting amplifier 216. The adjustment circuit 212, such as an analog-to-digital converter with frequency interpolation, generates an analog adjustment voltage by inputting a digital control signal. In other words, the first adjustment circuit 211 may generate a first analog adjustment voltage and the second adjustment circuit 212 may generate a second analog adjustment voltage.

The oscillator circuit, such as a ring oscillator, can adjust the level of the analog adjustment voltage. In other words, the first oscillator circuit 213 is configured to adjust the first analog adjustment voltage, and the second oscillator circuit 214 adjusts the second analog adjustment voltage. The decision circuit 215, such as a multiplexer, is configured to receive a data signal and an analog adjustment voltage (such as a first analog adjustment voltage or a second analog adjustment voltage). The decision circuit 215 then decides whether to transmit the designated data signal, such as data being 0 or data being 1, according to the analog adjustment voltage. The transmitting amplifier 216, such as a power amplifier, amplifies the data signal to be transmitted.

With reference to FIG. 1, FIG. 2 and FIG. 4, the receiver circuit 23 includes a front-end circuit 230, a follower circuit 240, a quadrature delay line 250 and an output circuit 260. The front-end circuit 230 includes a local amplification component 231, a local oscillator circuit 232, a first mixing component 233 and a second mixing component 234. Specifically, the local amplification component 231 (such as a low-noise amplifier) can receive and amplify the discontinuous signal to reduce the frequency of the discontinuous signal and filter out the high-frequency polarization voltage and the DC offset. The local oscillator circuit 232 generates an in-phase oscillation signal (for example,) 0° and a quadrature oscillation signal (for example, 90°). The term "in-phase" described in this specification means that the phase angle of the RF signal approaches 0°, such as 345° to 25°, preferably 340° to 20°, preferably 345° to 15°, preferably 350° to 10°, preferably 355° to 5°. The term "orthogonal" described in this specification means that the quadrature oscillation signal leads or lags the in-phase oscillation signal by a predetermined angle, such as 0° to 180°, preferably 0° to 90°, preferably 70° to 110°, preferably 80° to 100°, preferably 85° to 95°. However, the term "angle" is a directional term based on the signal transmission direction in the drawings and is not intended to limit the scope of this disclosure. The relative position between the elements is similar to that of the drawings and falls within the scope of this disclosure.

The first mixing component 233 can synthesize the discontinuous signal from the local amplification component 231 and in-phase oscillation signal from the local oscillator circuit 232 to output an in-phase signal (such as an in-phase baseband signal). The second mixing component 234 can synthesize the discontinuous signal from the local amplification component 231 and the quadrature oscillation signal from the local oscillator circuit 232 to output an quadrature signal (such as a quadrature baseband signal). The quadrature signal may lead or lag the in-phase signal by, for example, 90°. For example, when the front-end circuit 230 receives two discontinuous signals, namely, a first discontinuous signal with a frequency of 105 MHz and a second discontinuous signal with a frequency of 95 MHz, the first discontinuous signal and the second discontinuous signals may be modulated into an in-phase signal being +5 MHz (5∠0°) and a quadrature signal being −5 MHz (5∠270° or 5∠−90° that are orthogonal to each other and have zero intermediate frequency.

The front-end circuit 230 further includes a first amplification circuit 235 and a second amplification circuit 236. The first amplification circuit 235 amplifies the in-phase signal and filters out the high-frequency polarization voltage and the DC offset in the in-phase signal, and then the first amplification circuit 235 outputs an in-phase baseband signal. The second amplification circuit 236 amplifies the quadrature signal, filters out the high-frequency polarization voltage and the DC offset in the quadrature signal, and then the second amplification circuit 236 outputs a quadrature baseband signal.

The follower circuit 240 includes an in-phase delay line 241 and a feedback circuit 242, such as a delay locked loop (DLL). The in-phase delay line 241 may output a follower signal after the in-phase baseband signal is rotated by a phase angle. The feedback circuit 242 generates a control voltage after receiving the in-phase baseband signal and the follower signal, and feeds back the control voltage to the in-phase delay line 241 such that the in-phase delay line 241 enables the follower signal to follow the in-phase baseband signal according to the control voltage. The term "follow" described in this specification means that the in-phase delay line 241 controls the phase angle of the follower signal gradually approximates the phase angle of the in-phase baseband signal according to the control voltage, whereby the phase difference between the follower signal and the in-phase baseband signal remains less than a predetermined cycle, such as ±2π or ±3π. For example, the bandwidth of the delay locked loop is 1 MHz. The delay locked loop can lock the phase angle of the follower signal when the follower signal is in phase with the in-phase baseband signal in a cycle of 1 μs. When the in-phase baseband signal received by the in-phase delay line 241 and the feedback circuit 242 is discontinuous, for example, the data signal is switched between 1 and 0, the delay locked loop unlocks the phase angle of the follower signal and then detects a predetermined cycle range of the in-phase baseband signal, such as two cycles of the in-phase baseband signal, for example, 5 MHz. For example, if the phase difference between the follower signal and the in-phase baseband signal is 180°, the control voltage generated by the feedback circuit 242 is 0.2 volts.

Then, the in-phase delay line 241 detects two cycles of the in-phase baseband signal, for example, 5 MHz, according to 0.2 volts and corrects the phase angle of the in-phase baseband signal to 108° such that the phase difference between the follower signal and the in-phase baseband signal is 72°.

The in-phase delay line 241 may be, but not limited to, one or more D-type flip-flops. Each D-type flip-flop includes one or more input terminals and an output terminal. For example, a D-type flip-flop has two input terminals and two output terminals. When a plurality of D-type flip-flops is connected in series, two input terminals of a current D-type flip-flop are connected in series with the two output terminals of a previous stage.

The feedback circuit 242 includes a comparator component 243, a charge pump 244 and a converter circuit 129. The comparator component 243, for example, a phase frequency detector, is configured to compare the phase angle of the in-phase baseband signal with the phase angle of the follower signal to correspondingly generate a comparison signal. The charge pump 244, such as a multi-stage voltage doubler circuit, is configured to amplify the comparison signal and output a control current. The converter component 245, such as a first-order low-pass filter or a capacitor, is configured to convert the control current into a control voltage, and feedback the control voltage to the in-phase delay line 241 (such as an input terminal of a D-type flip-flop).

The quadrature delay line 250 may be, but is not limited to, one or more D-type flip-flops. Considering the matching between the D-type flip-flops and the follower circuit 240, i.e., the matching between the in-phase delay line 241 and the quadrature delay line 250, the circuit configurations of the quadrature delay line 250 and the in-phase delay line 241 are substantially the same. The difference between the quadrature delay line 250 and the in-phase delay line 241 is that the output terminal of the quadrature delay line 250 and the output terminal of the in-phase delay line 241 may be connected together to the same output circuit 260, to which, however, the scope of this disclosure is not limited. In one embodiment, there is a plurality of output circuits 260. For example, there are two output circuits 260. An output terminal of the quadrature delay line 250 is connected to an output circuit 260 and an output terminal of the in-phase delay line 241 is connected to another output circuit 260.

The output circuit 260 is a frequency-mixing component 261, such as a frequency-mixer. The frequency-mixing component 261 can synthesize the follower signal and the rotated quadrature baseband signal to output a synthesized signal. When the data signal is 1 and the phase difference between the follower signal and a rotary signal is 0°, the synthesized signal outputted by the frequency-mixing component 261 is 1. That is, the demodulated data signal is 1. On the contrary, when the data signal is 0 and the phase difference between the follower signal and the rotary signal is 180°, the synthesized signal outputted by the frequency-mixing component 261 is 0. That is, the demodulated data signal is 0.

In one embodiment, the synthesized signal includes a high frequency signal and a data signal, and the output circuit 260 includes a frequency-mixing component 261 and a filter component 262 connected to the frequency-mixing component 261. The filter component 262 may be, but is not limited to, a first-order or high-order low-pass filter, such as a Butterworth filter (Sallen-Key filter) that can receive and filter out harmonic signals at twice the baseband frequency of the synthesized signal, for example 10 Hz, to suppress the harmonic signal 35 dB. The filter component 262 can receive the synthesized signal from the frequency-mixing component 261. Then, the filter component 262 can filter out the high-frequency signal in the synthesized signal and output the data signal. In other words, the filter component 262 can output the data signal in the synthesized signal.

With reference to FIG. 2 to FIG. 5, a second embodiment of this disclosure provides a physiological information collecting system 1 including a portable electronic device 40 and a wearable electronic device 50. The portable electronic device 40 includes a communication interface 20, a user interface (such as a touch panel or a touch button) and a control component 25 connecting the communication interface 20 and the user interface. The user interface is configured to generate a trigger signal. The control component 25 drives the communication interface 20 to modulate the data signal into the discontinuous signal according to the touch signal, and transmit the discontinuous signal. The user interface may be, but is not limited to, a panel with a capacitive touch sensor. When the user touches the panel, the capacitive touch sensor detects the position where the panel is touched and generates a trigger signal. The control component 25 executes an application corresponding to the position where the panel is touched according to the trigger signal, and then the application can transmit a discontinuous signal containing a wake-up signal to the receiver circuit 23 of the wearable electronic device 50. After the receiver circuit 23 of the wearable electronic device 50 demodulates the wake-up signal in the discontinuous signal containing the wake-up signal, the transmitter circuit 21 of the wearable electronic device 50 transmits a discontinuous signal containing the data signal to the communication interface 20 of the portable electronic device 40 according to the wake-up signal. Then, the communication interface 20 of the portable electronic device 40 demodulates the data signal in the discontinuous signal containing the data signal.

The wearable electronic device 50 includes a transmitter circuit 21, a receiver circuit 23 and a control component 25. The transmitter circuit 21 can transmit a discontinuous signal containing a wake-up signal to drive the communication interface 20 of the portable electronic device 40 to transmit a discontinuous signal containing a data signal to the receiver circuit 23 of the wearable electronic device 50. The receiver circuit 23 receives the discontinuous signal containing the data signal and demodulates the data signal in the discontinuous signal containing the data signal. Then, the control component 25 drives the transmitter circuit 21 to transmit a discontinuous signal containing a sleep signal to drive the communication interface 20 of the portable electronic device 40 to stop transmitting the discontinuous signal containing the data signal.

In one embodiment, the portable electronic device 40 includes a storage unit configured to receive and store a data signal. The wearable electronic device 50 includes a storage element configured to receive and store the data signal. The storage unit and the storage element have been disclosed in the storage components described above, and descriptions thereof are not to be repeated herein.

In one embodiment, the communication interface 20 of the portable electronic device 40 can obtain the ID number of the wearable electronic device 50 via a protocol, such as TCP, HTTP, SSL, or the like. On the contrary, the communication interface 20 of the wearable electronic device 50 may also obtain the ID number of the portable electronic device 40 via a protocol. That is, the portable electronic device 40 and the wearable electronic device 50 establish a connection to each other via the handshake process.

In one embodiment, the physiological information collecting system 1 further includes a detection device 100. The detection device 100 includes a detection module 11 and a communication module 12. The communication interface (such as a transmitter circuit 21) of the portable electronic device 40 or the wearable electronic device 50 may transmit a discontinuous signal containing a wake-up signal to the communication module 12 of the detection device 100. The detection module 11 demodulates the wake-up signal in the discontinuous signal and transmits a discontinuous signal containing the data signal to the portable electronic device 40 or the receiver circuit 23 of the wearable electronic device 50 according to the wake-up signal. Then, the receiver circuit 23 demodulates the data signal in the discontinuous signal.

In one embodiment, when the transmitter circuit 21 of the wearable electronic device 50 transmits a discontinuous signal containing a wake-up signal, the communication module 12 of the detection device 100 or the communication interface (such as a transmitter circuit 21) of the portable electronic device 40 can receive the discontinuous signal containing the wake-up signal and demodulate the wake-up signal in the discontinuous signal, and transmit a discontinuous signal containing a data signal to the receiver circuit 23 of the wearable electronic device 50 according to the wake-up signal. Next, the receiver circuit 23 of the wearable electronic device 50 can receive the discontinuous signal containing the data signal transmitted from the communication interface 20 of the portable electronic device 40 or the discontinuous signal containing the data signal transmitted from the communication module 12 of the detection device 100.

In one embodiment, when a communication interface (such as the sending circuit 21) of the portable electronic device 40 transmits a discontinuous signal containing a wake-up signal, the communication module 12 of the detection device 100 or the receiver circuit 23 of the wearable electronic device 50 can demodulate the wake-up signal in the discontinuous signal containing the wake-up signal. Next, the communication module 12 of the detection device 100 or the transmitter circuit 21 of the wearable electronic device 50 transmits a discontinuous signal containing a data signal to the communication interface 20 (such as a receiver circuit 23) of the portable electronic device 40 according to the wake-up signal. Then, the communication interface 20 (such as a receiver circuit 23) of the portable electronic device 40 can demodulate the discontinuous signal containing the data signal transmitted by the transmitter circuit 21 of the wearable electronic device 50 or the communication module 12 of the detection device 100.

In one embodiment, the communication module 12 of the detection device 100 may obtain the ID number of the wearable electronic device 50 or the ID number of the portable electronic device 40 via a protocol such as TCP, HTTP, SSL, etc. ID number. Similarly, the communication interface 20 of the portable electronic device 40 or the communication interface 20 of the wearable electronic device 50 can also obtain the ID number of the portable electronic device 40 via an internet protocol. In other words, the detection device 100, the portable electronic device 40 and the wearable electronic device 50 establish a connection between any two or three parties through a handshake process.

Through one or more embodiments of this disclosure, the detection device 100 and the transceiver device 200 may receive or transmit a modulated signal (such as a continuous signal or a discontinuous signal) via the human body passage because the human body passage provides a wider bandwidth compared to RF bandwidth. However, when the detection device 100 and the transceiver device 200 transmit a continuous signal, the detection device 100 and the transceiver device 200 consume a large amount of power. Therefore, the detection device 100 and the transceiver device 200 are adapted to transmit the discontinuous signal to reduce the power consumption and simplify the circuit configurations of the detection device 100 and the transceiver device 200. Additionally, the detection device 100 and the transceiver device 200 reduce the bandwidth range of the discontinuous signal when transmitting the discontinuous signal, reduce the power consumed by the detection device 100 and the transceiver device 200, and demodulate the discontinuous signal with various transmission rates of different data.

While this disclosure has been described by the way of example and in terms of the preferred embodiments, it is to be understood that the invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. A physiological information collecting system, comprising:
  a detection device, comprising:
    a detection module configured to detect a data signal; and
    a communication module configured to modulate said data signal into a discontinuous signal and transmit said discontinuous signal; and
  a transceiver device, comprising:
    a front-end circuit configured to receive and amplify said discontinuous signal and separate said discontinuous signal amplified into an in-phase baseband signal and a quadrature baseband signal that are orthogonal to each other;
    a follower circuit configured to output a control voltage and configured to rotate said in-phase baseband signal by a phase angle to output a follower signal, said follower signal following said in-phase baseband signal, and said control voltage corresponding to a phase angle difference between said follower signal and said in-phase baseband signal;
    a quadrature delay line configured to rotate said quadrature baseband signal by a corresponding phase angle according to said control voltage, said corresponding phase angle being said phase angle difference plus 90 degrees; and
    an output circuit configured to synthesize said follower signal and said quadrature baseband signal rotated and output said data signal;
  wherein said follower circuit comprises:
    an in-phase delay line configured to output said follower signal after rotating said in-phase baseband signal by said phase angle; and
    a feedback circuit configured to output said control voltage after receiving said in-phase baseband signal and said follower signal such that said in-phase delay line receives said control voltage;
    wherein said in-phase delay line enables said follower signal to follow said in-phase baseband signal according to said control voltage;
  wherein said feedback circuit comprises:

a comparator component configured to compare said phase angle of said in-phase baseband signal and said phase angle of said follower signal to correspondingly generate a comparison signal;

a charge pump configured to amplify said comparison signal and output a control current; and a converter component configured to convert said control current into said control voltage.

2. The physiological information collecting system according to claim 1, wherein said transceiver device is a wearable electronic device or a portable electronic device.

3. The physiological information collecting system according to claim 1, wherein said detection device further comprises a first touch element electrically connected to said communication module, and said transceiver device further comprises a second touch element electrically connected to said front-end circuit.

4. The physiological information collecting system according to claim 1, wherein said transceiver device comprises an input component configured to drive said communication module to transmit said discontinuous signal.

5. The physiological information collecting system according to claim 1, wherein said output circuit comprises:
   a frequency-mixing component configured to synthesize said follower signal and said quadrature baseband signal rotated; and
   a filter component configured to filter and output said data signal.

6. The physiological information collecting system according to claim 1, wherein said transceiver device comprises a storage component configured to receive and store said data signal after said output circuit outputs said data signal.

7. The physiological information collecting system according to claim 1, wherein said detection device comprises a storage module configured to receive and store said data signal after said detection module detects said data signal.

8. The physiological information collecting system according to claim 1, wherein said front-end circuit comprises:
   a local amplification component configured to receive and amplify said discontinuous signal;
   a local oscillator circuit configured to generate an in-phase oscillation signal and a quadrature oscillation signal;
   a first mixing component configured to synthesize said discontinuous signal amplified and said in-phase oscillation signal and output said in-phase baseband signal;
   a second mixing component configured to synthesize said discontinuous signal amplified and said quadrature oscillation signal and output said quadrature baseband signal;
   a first amplification circuit configured to amplify said in-phase baseband signal; and
   a second amplification circuit configured to amplify said quadrature baseband signal.

9. A transceiver device, comprising:
   a front-end circuit configured to receive and amplify a discontinuous signal and separate said discontinuous signal amplified into an in-phase baseband signal and a quadrature baseband signal that are orthogonal to each other;
   a follower circuit configured to output a control voltage and configured to rotate said in-phase baseband signal by a phase angle to output a follower signal, said follower signal following said in-phase baseband signal, and said control voltage corresponding to a phase angle difference between said follower signal and said in-phase baseband signal;
   a quadrature delay line configured to rotate said quadrature baseband signal by a corresponding phase angle according to said control voltage, said corresponding phase angle being said phase angle difference plus 90 degrees; and
   an output circuit configured to synthesize said follower signal and said quadrature baseband signal rotated and output a data signal;
   wherein said follower circuit comprises:
      an in-phase delay line configured to output said follower signal after rotating said in-phase baseband signal by said phase angle; and
      a feedback circuit configured to output said control voltage after receiving said in-phase baseband signal and said follower signal such that said in-phase delay line receives said control voltage;
      wherein said in-phase delay line enables said follower signal to follow said in-phase baseband signal according to said control voltage;
   wherein said feedback circuit comprises:
      a comparator component configured to compare said phase angle of said in-phase baseband signal and said phase angle of said follower signal to correspondingly generate a comparison signal;
      a charge pump configured to amplify said comparison signal and output a control current; and
      a converter component configured to convert said control current into said control voltage.

10. The transceiver device according to claim 9, further comprising a second storage component configured to receive and store said data signal.

11. The transceiver device according to claim 9, wherein said transceiver device is a wearable electronic device or a portable electronic device.

12. The transceiver device according to claim 9, further comprising a touch element electrically connected to said front-end circuit.

13. The transceiver device according to claim 9, further comprising an input component configured to drive said front-end circuit to receive said discontinuous signal.

14. The transceiver device according to claim 9, wherein said output circuit comprises:
   a frequency-mixing component configured to synthesize said follower signal and said quadrature baseband signal rotated; and
   a filter component configured to filter and output said data signal.

15. The transceiver device according to claim 9, wherein said front-end circuit comprises:
   a local amplification component configured to receive and amplify said discontinuous signal;
   a local oscillator circuit configured to generate an in-phase oscillation signal and a quadrature oscillation signal;
   a first mixing component configured to synthesize said discontinuous signal amplified and said in-phase oscillation signal and output said in-phase baseband signal;
   a second mixing component configured to synthesize said discontinuous signal amplified and said quadrature oscillation signal and output said quadrature baseband signal;
   a first amplification circuit configured to amplify said in-phase baseband signal; and a second amplification circuit configured to amplify said quadrature baseband signal.

16. A physiological information collecting system, comprises:
- a portable electronic device, comprising:
  - a touch element configured to generate a touch signal; and
  - a communication interface configured to modulate a data signal into a discontinuous signal and transmit said discontinuous signal according to said touch signal; and
- a wearable electronic device, comprising:
  - a front-end circuit configured to receive and amplify said discontinuous signal transmitted by said communication interface and separate said discontinuous signal amplified into an in-phase baseband signal and a quadrature baseband signal that are orthogonal to each other;
  - a follower circuit configured to output a control voltage and configured to rotate said in-phase baseband signal by a phase angle to output a follower signal, said follower signal following said in-phase baseband signal, and said control voltage corresponding to a phase angle difference between said follower signal and said in-phase baseband signal;
  - a quadrature delay line configured to rotate said quadrature baseband signal by a corresponding phase angle according to said control voltage, said corresponding phase angle being said phase angle difference plus 90 degrees; and
  - an output circuit configured to synthesize said follower signal and said quadrature baseband signal rotated and output said data signal;
- wherein said follower circuit comprises:
  - an in-phase delay line configured to output said follower signal after rotating said in-phase baseband signal by said phase angle; and
  - a feedback circuit configured to output said control voltage after receiving said in-phase baseband signal and said follower signal such that said in-phase delay line receives said control voltage;
  - wherein said in-phase delay line enables said follower signal to follow said in-phase baseband signal according to said control voltage;
- wherein said feedback circuit comprises:
  - a comparator component configured to compare said phase angle of said in-phase baseband signal and said phase angle of said follower signal to correspondingly generate a comparison signal;
  - a charge pump configured to amplify said comparison signal and output a control current; and
  - a converter component configured to convert said control current into said control voltage.

17. The physiological information collecting system according to claim 16, wherein said wearable electronic device and said portable electronic device comprise a storage component, respectively, configured to store said data signal.

18. The physiological information collecting system according to claim 16, wherein said portable electronic device comprises:
- a control component configured to drive said communication interface to modulate said data signal into said discontinuous signal and transmit said discontinuous signal to said front-end circuit after said communication interface receives said touch signal and said data signal.

19. The physiological information collecting system according to claim 16, further comprising:
- a detection device, comprising:
  - a detection module configured to detect said data signal; and
  - a communication module configured to modulate said data signal into said discontinuous signal and transmit said discontinuous signal;
- wherein said front-end circuit is configured to receive said discontinuous signal transmitted by said communication module or said discontinuous signal transmitted by said communication interface when said communication module or said communication interface is configured to transmit said discontinuous signal.

20. The physiological information collecting system according to claim 19, wherein said communication interface or said front-end circuit is configured to receive said discontinuous signal when said communication module is configured to transmit said discontinuous signal.

21. The physiological information collecting system according to claim 19, wherein said detection device comprises a storage module configured to store said data signal after said detection module detects said data signal.

22. The physiological information collecting system according to claim 19, further comprising a first touch element electrically connected to said communication module and a second touch element electrically connected to said front-end circuit.

23. The physiological information collecting system according to claim 16, wherein said output circuit comprises:
- a frequency-mixing component configured to synthesize said follower signal and said quadrature baseband signal rotated; and
- a filter component configured to filter and output said data signal.

24. The physiological information collecting system according to claim 16, wherein said front-end circuit comprises:
- a local amplification component configured to receive and amplify said discontinuous signal;
- a local oscillator circuit configured to generate an in-phase oscillation signal and a quadrature oscillation signal;
- a first mixing component configured to synthesize said discontinuous signal amplified and said in-phase oscillation signal and output said in-phase baseband signal;
- a second mixing component configured to synthesize said discontinuous signal amplified and said quadrature oscillation signal and output said quadrature baseband signal;
- a first amplification circuit configured to amplify said in-phase baseband signal; and
- a second amplification circuit configured to amplify said quadrature baseband signal.

* * * * *